United States Patent
MacDonald

(10) Patent No.: US 7,998,093 B2
(45) Date of Patent: Aug. 16, 2011

(54) INTERNAL NOSTRIL OR NASAL AIRWAY SIZING GAUGE

(75) Inventor: Louise S. MacDonald, Beverly, MA (US)

(73) Assignee: Sanostec, Corp., Beverly Farms, MA (US)

( * ) Notice: Subject to any disclaimer, the term of this patent is extended or adjusted under 35 U.S.C. 154(b) by 144 days.

(21) Appl. No.: 12/197,517

(22) Filed: Aug. 25, 2008

(65) Prior Publication Data

US 2009/0062694 A1    Mar. 5, 2009

Related U.S. Application Data

(60) Provisional application No. 60/957,851, filed on Aug. 24, 2007.

(51) Int. Cl.
*A61B 5/00* (2006.01)
*A61B 5/103* (2006.01)
*A61B 5/107* (2006.01)
*G01B 3/34* (2006.01)
*G01B 5/06* (2006.01)
*G01B 5/08* (2006.01)

(52) U.S. Cl. ............ 600/587; 33/511; 33/512; 33/514.1
(58) Field of Classification Search ............... 600/587; 33/494, 511, 512, 514.1, 555.2, 679.1
See application file for complete search history.

(56) References Cited

OTHER PUBLICATIONS

Berger, Eric, "SciGuy A science blog with Eric Berger—Answer this question, win a book", Mar. 13, 2006, blogs.chron.com/sciguy/archives/2006/03/answer_this_que.html, pp. 1-5.*

* cited by examiner

*Primary Examiner* — Max Hindenburg
*Assistant Examiner* — Emily M Lloyd
(74) *Attorney, Agent, or Firm* — Nutter McClennan & Fish LLP

(57) ABSTRACT

Methods of sizing a nasal airway by using certain measurements of digits may include (a) pressing a distal portion of a digit of a hand against a resilient, flat surface, such that flesh of the distal portion of the digit spreads laterally on the surface; (b) measuring the digit's width at a digit measuring level, the measuring level being the widest part of the digit distal to a distal-most interphalangeal joint of the digit; and (c) identifying a nasal airway size as that size which correlates most closely to the digit's width as measured at the digit measuring level.

14 Claims, 1 Drawing Sheet

Fig. 1
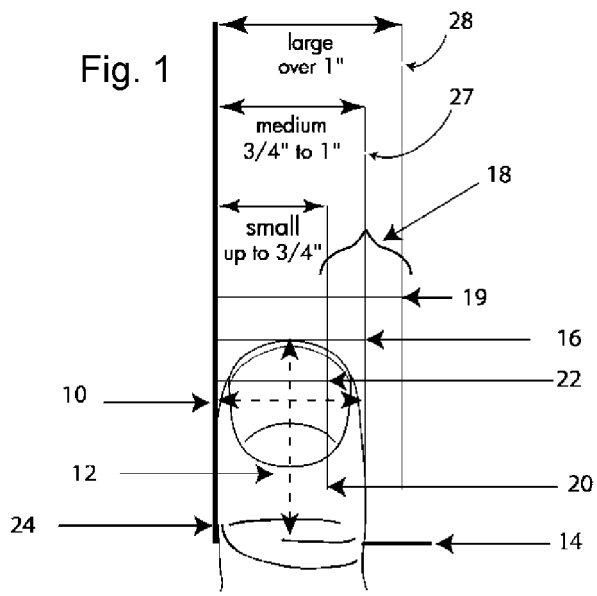
Fig. 2
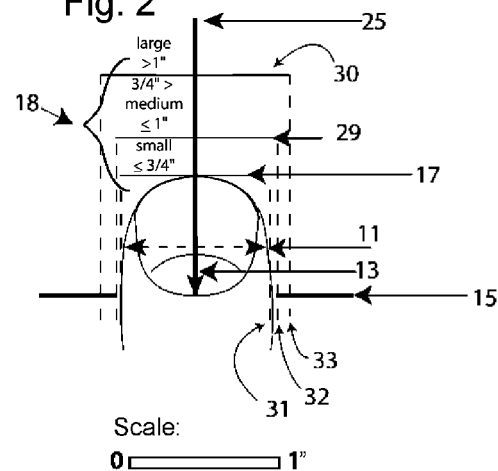
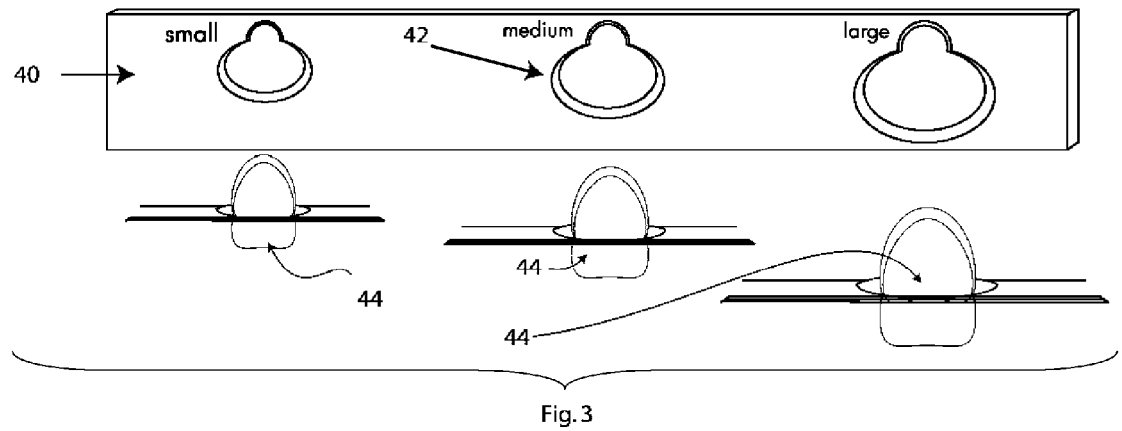
Fig. 3
Fig. 4 (prior art)
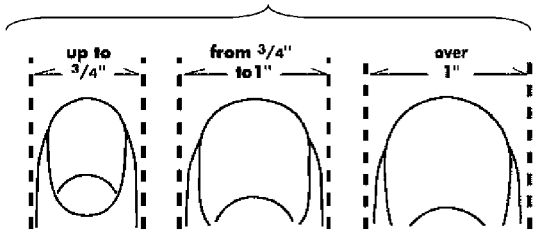

INTERNAL NOSTRIL OR NASAL AIRWAY SIZING GAUGE

CROSS-REFERENCE TO RELATED APPLICATION

This application claims the benefit of U.S. Provisional Application No. 60/957,851, filed Aug. 24, 2007, which is hereby incorporated herein by reference.

BACKGROUND

1. Field of the Invention:

The size of a nostril, or of a nasal airway, may be gauged by using certain measurements of digits (particularly the thumb, the fifth digit, and the other digits of the hand). Those measurements may be carried out using a sizing gauge, such as one that includes sizing lines indicating a variety of distinct sizes. The sizing lines may indicate widths that overlie one another, so that a user trying to gauge airway size need not move the digit between separate gauges.

2. Description of Related Art:

The internal nostril or nasal airway-sizing guides disclosed herein facilitate accurate measurement of certain dimensions of an individual's digits. Such accurate measurement is useful, for example, to gauge the internal measurement of the nostril or nasal airway, and to use that measurement to select the appropriate size nasal insert, such as those described in U.S. Pat. No. 6,562,057, which document is hereby incorporated herein by reference.

The inventor has discovered that certain dimensions of an individual's digits can be correlated to certain dimensions of an individual's internal nostril, or nasal airway size. Gauging the size of an individual's internal nostril or nasal airway by measuring certain dimensions of their digit(s) provides a highly correlating sizing method that is much easier, faster and more convenient than measuring the nostril or nasal airway directly.

In particular, the widest part of the digit distal to the distal-most interphalangeal joint of the digit correlates surprisingly well with airway size. (The widest part typically occurs somewhere below the margin of the nail.)

Thumb-based sizing gauge nostril size prediction is known in the art; an example of a prior-art thumb-based sizing guide is shown in FIG. 4. While this guide is effective, certain improvements, disclosed herein, can significantly improve accuracy and determine repeatability of sizing. The prior-art guide includes three side-by-side silhouettes: one each for small, medium, and large sized-thumbs. To assess size, a user places the thumb over one of the silhouettes and judges whether the thumb is larger than, smaller than, or about the same size as the silhouette. If larger or smaller, the user tries another silhouette and ultimately tries to select the size whose silhouette best correlates to the thumb size.

This prior art guide suffers from at least two disadvantages: it does not specify the exact place of width measure, which causes errors in judgment as to which width of measure to use because the user must move back and forth between the silhouettes trying to determine how best to match which part of their digit; and, it does not make any measure of length. The lack of a measure for a specific length causes errors in judgments as to which length is best correlated to the most appropriate fit.

The sizing gauges and methods disclosed herein address these two disadvantages.

SUMMARY

For example, a method of sizing a nasal airway may include (a) pressing a distal portion of a digit of a hand against a resilient, flat surface, such that flesh of the distal portion of the digit spreads laterally on the surface; (b) measuring the digit's width at a digit measuring level, the measuring level being the widest part of the digit distal to a distal-most interphalangeal joint of the digit; and (c) identifying a nasal airway size as that size which correlates most closely to the digit's width as measured at the digit measuring level.

Sizing lines may be marked on the surface where the digit is pressed to simplify the measurement. Multiple overlaid width sizing lines corresponding to widths different from one another are marked on the surface, the digit is pressed against the surface where the lines are marked, and the nasal airway size is identified as correlating to the sizing line indicating the narrowest width that is not obscured by the digit.

A proximal-distal line may be marked on the surface, relative to which the sizing lines are marked, and the digit may be positioned relative to the proximal-distal line.

The sizing lines may be positioned so that they are centered on the proximal-distal line, and the digit may be positioned so that it is centered on the proximal-distal line.

The sizing lines may be all positioned to one side of the proximal-distal line, and the digit may be positioned so that the flesh at the digit measuring level extends to the proximal-distal line.

A base line orthogonal to the proximal-distal line may be marked on the surface, and the digit may be positioned relative to the base line. The digit may be positioned so that the digit measuring level or the distal-most interphalangeal joint overlies the base line. A digit length from the base line to a distal tip of the digit may be measured when the digit is so positioned.

BRIEF DESCRIPTION OF THE DRAWINGS

FIG. 1 depicts one exemplary embodiment of an internal nostril, or nasal airway-sizing gauge.

FIG. 2 depicts another exemplary embodiment of a sizing gauge that may be used in measuring a certain dimension of a digit to aid in determining the size of an internal nostril, or nasal airway, and using that measure to correlate to the measure of a nasal device.

FIG. 3 depicts another exemplary embodiment of a holed sizing gauge that may be used in measuring a certain dimension of a digit to aid in determining the size of an internal nostril, or nasal airway, and using that measure to correlate to the measure of a nasal device.

FIG. 4 depicts a prior-art sizing guide.

DETAILED DESCRIPTION

FIG. 1 depicts a first exemplary embodiment of a sizing gauge. This gauge helps a person select a size based on both digit width (dotted line 10) and length (dotted line 12). It includes a base line 14 on which a user's thumb interphalangeal joint is aligned, and a proximal-distal line (edge line 24) against which the thumb side is be aligned (as shown by the example thumb in the figure). A series incremental width lines (20, 27, 28) and length lines (22, 16, 19) extend parallel to the side and base lines, respectively. These lines form an incremental scale 18. When a user places a thumb on the gauge in this manner, the thumb will obscure measures that are too small.

In using the gauge illustrated in FIG. 1, the person is instructed to (1) place the thumb on the gauge so that the bottom edge of the knuckle is aligned with the base line 14, and the left edge of the thumb is aligned with the edge line 24, as demonstrated in the figure, and (2) gauge the thumb size by using the lines that are visible and that are closest to the thumb. The user can more clearly assess whether a thumb edge is closer to one line than to another without having to move thumb off the gauge.

FIG. 2 depicts a second exemplary embodiment of a sizing gauge. This gauge similarly helps a person select a size based on both digit width (dotted line 11) and length (line 13). This gauge includes a base line 15 over which the bottom of the user's thumbnail is aligned, and proximal-distal line (centerline 25) about which the thumb is centered (as shown by the example thumb in the figure). A series of incremental width lines (31, 32, 33) and length lines (17, 29, 30) extend parallel to the side and centerlines, respectively. These lines form an incremental scale 18. When a user places a thumb on the gauge in this manner, the thumb will obscure measures that are too small.

In using the gauge illustrated in FIG. 2, the person is instructed to (1) place the thumb on the gauge so that the bottom edge of the thumbnail is aligned over the horizontal base line 15, and the center of the thumb is aligned over the centerline 25, as demonstrated in this illustration, and (2) gauge the thumb size by using the lines that are visible and that are closest to the thumb.

The method does not necessarily require use of a surface on which sizing lines are marked. For example, a separate measuring device (such as calipers or a card with holes) may be laid against or fitted on the digit to make the measurement.

Pressing the digit so that the flesh bulges (spreads laterally) helps accentuate the digit's shape and make the widest part more readily apparent. Pressing may not be necessary if the widest part of the digit is apparent without pressing.

The measuring indicators on the gauge may be raised, embossed or textured for aiding measurement.

The exemplary embodiments indicate only three sizes, but a gauge could indicate additional sizes. For example, the illustrated embodiments indicate small, medium, and large, but a gauge could also indicate extra-small and/or extra-large. Labels other than these may be used, such as narrow, intermediate, and wide, or short, average, and long, among others. Moreover, the gauge can permit separate width and length measurements to identify sizes in two dimensions (such as narrow-long, medium-medium, wide-short, etc.).

FIG. 3 depicts a third exemplary embodiment of a nasal airway-sizing gauge. This gauge similarly helps a person select a size based on just digit width. This gauge may be fashioned by using a length of stiff material 40, i.e. cardboard, plastic, metal or wood (much like a ruler) that has been precut through with holes of varying diameters 42, and that permit the through insertion of the end of the digit. The correct measure of width is determined by inserting the nail through the hole 44 most suited so that only the nail is visible on the far side of the length of material.

I claim:

1. A method of sizing a nasal airway using a sizing gauge comprising:

pressing a distal portion of a digit of a hand against a sizing gauge, the sizing gauge having a resilient, flat surface, such that flesh of the distal portion of the digit spreads laterally on the surface;

measuring the pressed digit's width at a digit measuring level, the measuring level being the widest part of the digit distal to a distal-most interphalangeal joint of the digit; and identifying a nasal airway size as that size which correlates to the digit's width as measured at the digit measuring level.

2. The method of claim 1, wherein the digit is a thumb.

3. The method of claim 1, wherein the sizing gauge includes multiple overlaid width sizing lines, corresponding to sizing widths different from one another, marked on the surface whereby when the digit is pressed against the surface where the lines are marked, the nasal airway size is identified as correlating to the sizing line indicating the narrowest sizing width that is not obscured by the digit.

4. The method of claim 3, wherein a proximal-distal line is marked on the surface, relative to which the sizing lines are marked, and the method further comprises positioning the digit relative to the proximal-distal line.

5. The method of claim 4, wherein the sizing lines are positioned so that they are centered on the proximal-distal line, and the digit is positioned so that the digit is centered on the proximal-distal line.

6. The method of claim 4, wherein the sizing lines are all positioned to one side of the proximal-distal line, and the method further comprises positioning the digit so that the flesh at the digit measuring level extends to the proximal-distal line.

7. The method of claim 4, further comprising a base line orthogonal to the proximal-distal line, and the method further comprises positioning the digit relative to the base line.

8. The method of claim 7, wherein the digit is positioned so that the digit measuring level overlies the base line.

9. The method of claim 7, wherein the digit is positioned so that the distal-most interphalangeal joint overlies the base line.

10. The method of claim 7, further comprising measuring a digit length from the base line to a distal tip of the digit.

11. The method of claim 1, wherein the digit is a fifth digit.

12. A method of sizing a nasal airway using a sizing gauge having a plurality of holes comprising:

inserting a digit into a hole formed in a sizing guide, the sizing guide having a plurality of holes of varying diameters that permit a through insertion of the end of a digit; and identifying a nasal airway size as that size which correlates most closely to the smallest of the holes through which the digit can be inserted no further than the digit's nail base.

13. The method of claim 12, wherein the digit is a thumb.

14. The method of claim 12, wherein the digit is a fifth digit.

* * * * *